United States Patent
Javid (10) Patent No.: US 8,784,375 B2
(45) Date of Patent: Jul. 22, 2014

(54) SAFETY CARPULE SYSTEM WITH INTEGRAL RETRACTABLE NEEDLE

(76) Inventor: Hossein Javid, Inglewood, CA (US)

( * ) Notice: Subject to any disclaimer, the term of this patent is extended or adjusted under 35 U.S.C. 154(b) by 471 days.

(21) Appl. No.: 13/152,217

(22) Filed: Jun. 2, 2011

(65) Prior Publication Data

US 2012/0310160 A1    Dec. 6, 2012

(51) Int. Cl.
*A61M 5/00*    (2006.01)
(52) U.S. Cl.
USPC ......................................................... 604/110
(58) Field of Classification Search
USPC ......... 604/150, 110, 196, 111, 195, 192, 410, 604/88, 181, 232, 506, 198, 187, 90
See application file for complete search history.

(56) References Cited

U.S. PATENT DOCUMENTS

| | | | |
|---|---|---|---|
| 4,826,489 A | 5/1989 | Haber et al. | |
| 4,929,230 A | 5/1990 | Pfleger | |
| 4,931,040 A | 6/1990 | Haber et al. | |
| 5,116,319 A * | 5/1992 | van den Haak | 604/110 |
| 5,269,766 A | 12/1993 | Haber et al. | |
| 5,330,440 A * | 7/1994 | Stanners et al. | 604/195 |
| 5,358,491 A | 10/1994 | Johnson et al. | |
| 6,808,511 B2 | 10/2004 | Pond | |
| 7,267,668 B2 | 9/2007 | Ruben | |
| 2003/0212366 A1 * | 11/2003 | Bang | 604/196 |

* cited by examiner

*Primary Examiner* — Nicholas D Lucchesi
*Assistant Examiner* — Brooke Matney
(74) *Attorney, Agent, or Firm* — Lance M. Pritikin, Esq.

(57) ABSTRACT

A safety carpule system with integral retractable needle includes a piston element disposed between a needle hub assembly and a plunger element, each being axially slideable within a cylindrical housing. A medication-filled fluid chamber is defined between the plunger element and the piston element. The piston element is forced to into a fluid release position by way of an increase in fluid pressure within the fluid chamber, which in turn is caused by actuation of the plunger element toward the needle hub assembly by way of a syringe plunger rod. When the piston element is in fluid release position, the medication is able to flow from the fluid chamber through the needle as the syringe plunger rod is further compressed. Once the carpule system is spent, the piston element is latchably engaged by both the needle hub assembly and the plunger element, thus allowing the needle to be fully retracted into the housing upon return of the syringe plunger rod to its extended position. The spent carpule system with retracted needle is then conveniently removable from the syringe barrel for safe handling and disposal.

20 Claims, 7 Drawing Sheets

SAFETY CARPULE SYSTEM WITH INTEGRAL RETRACTABLE NEEDLE

RELATED APPLICATIONS

Not applicable.

TECHNICAL FIELD

The present invention relates generally to medication carpules adapted to be used in connection with medical and dental syringe systems. More particularly, the invention concerns a disposable carpule system with an integral retractable needle, wherein medication can be dispensed from the carpule and the needle retracted from exposure by way of the syringe plunger rod.

BACKGROUND OF THE INVENTION

Disposable carpules filled with a liquid medication are commonly used in connection with medical and dental syringe systems. In many such conventional systems, after the medication is dispensed, the injection needle remains dangerously exposed, either as part of the spent carpule or as a component attached to the syringe barrel. As a result, the used needle of a conventional injection system must typically be recapped or cautiously removed from the syringe, and handled and disposed of with extreme care. Those in the art recognize the need for a safer and more convenient medication carpule system, particularly one that is pre-filled with a selected liquid medication, includes the injection needle as an integral part of a carpule system, and in which the injection needle can be easily retracted from unsafe exposure once the medication is dispensed and prior to removal of the carpule system from the syringe.

SUMMARY OF THE INVENTION

By way of summary, a safety carpule system with integral retractable needle generally includes a housing element, a needle hub assembly, a plunger element and a piston element. The housing element is substantially cylindrical and includes a first end, a second end and a main bore extending axially therebetween. The main bore has a radial wall. The needle hub assembly includes a needle element extending through a hub element. The needle hub assembly is axially transportable within the main bore between an injection position and a retracted position. A forward portion of the needle element extends outwardly of the first end when the needle hub assembly is in its injection position. The forward portion of the needle hub assembly is protected entirely within the housing element when the needle hub assembly is in its retracted position.

The plunger element is in sealing engagement with the main bore and is axially actuatable therewithin between a ready position, a capture position and a safety position. The piston element includes a diaphragm member and is disposed within the main bore generally between the needle hub assembly and the plunger element. A fluid chamber is generally defined by the volume within the main bore between the plunger element and the diaphragm member. The piston element is in sealing engagement with the radial wall and is axially movable from a fluid retaining position to a fluid release position. This axial movement occurs by way of an increase in a fluid pressure within the fluid chamber resulting from the actuation of the plunger element from its ready position toward its capture position. The piston element prevents fluid communication between the fluid chamber and the needle element when in its fluid retaining position. The diaphragm member is punctured and allows fluid communication between the fluid chamber and the needle element when the piston element is in its fluid release position. The piston element is simultaneously latchingly engageable by the needle hub assembly and the plunger element when the plunger element is in its capture position. As a result, the actuation of the plunger element from its capture position to its safety position results in the needle hub assembly being transported from its injection position to its retracted position.

The detailed description of embodiments of the safety carpule system with integral retractable needle is intended to serve merely as examples, and is in no way intended to limit the scope of the appended claims to these described embodiments. Accordingly, modifications to the embodiments described are possible, and as will be clearly understood by those skilled in the art, the invention may be practiced in many different ways than the embodiments specifically described below, and still remain within the scope of the claims.

BRIEF DESCRIPTION OF THE DRAWINGS

Further advantages of the present invention may become apparent to those skilled in the art with the benefit of the following detailed description of the preferred embodiments and upon reference to the accompanying drawings in which.

DETAILED DESCRIPTION OF THE PREFERRED EMBODIMENTS

Referring now to the drawings, like reference numerals designate identical or corresponding features throughout the several views.

Throughout the various figures, embodiments of a safety carpule system with integral retractable needle are shown generally at 100. A safety carpule system 100 may generally comprise a housing element 102, a needle hub assembly 112, a plunger element 120 and a piston element 122. A housing element 102 may be substantially cylindrical and include a first end 104, a second end 106 and a main bore 108 extending axially therebetween. The main bore 108 has a radial wall 110. As illustrated, for example, in FIGS. 2, 3, 7 and 8, certain preferred embodiments of a safety carpule system 100 are adapted to be laterally loaded into and laterally unloaded from a breech-loadable syringe assembly 156. A breech-loadable syringe assembly 156 may have a syringe plunger rod 128 with a thumb ring 174, a syringe body 170, a slider element 176, and a syringe barrel 162 with a breech opening 168 and a proximal end 164. The breech opening 168 is typically adapted to substantially laterally receivingly engage the housing element 102.

Figure 16:
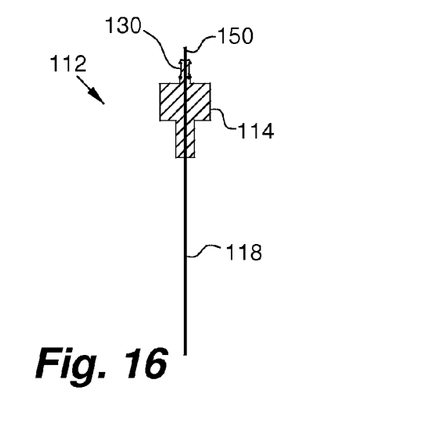
FIG. 16 is a diagrammatic cross-sectional view of the needle hub assembly shown in FIG. 15.

A needle hub assembly 112 may include a hub element 114 and a needle element 116 extending generally through the hub element 114. The needle hub assembly 112 is axially transportable within the main bore 108 between an injection position (as shown, for example, in FIG. 26) and a retracted position (as shown, for example, in FIG. 29). A forward portion 118 of the needle element 116 typically extends outward of the first end 104 when the needle hub assembly 112 is in the injection position. The forward portion 118 of the needle element 116 is typically disposed entirely within the housing element 102 when the needle hub assembly 112 is in the retracted position. As illustrated, for example, in FIGS. 16 and 26, in preferred embodiments, the housing element 102 includes a hub seat 152 for engaging a shoulder portion 154 of the hub element 114 to restrict axial movement of the hub element 114 outward of the first end 104 when the needle hub assembly 112 is in the injection position.

Figure 11:
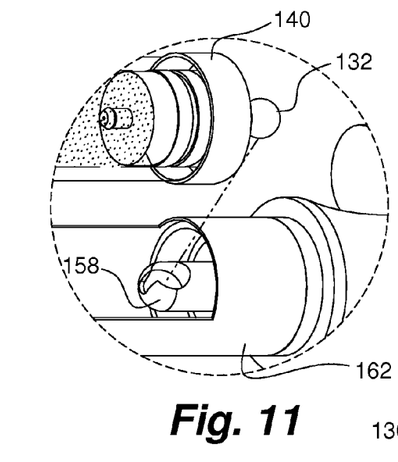
FIG. 11 is a diagrammatic enlarged view of detail 11 in FIG. 2.
Figure 12:
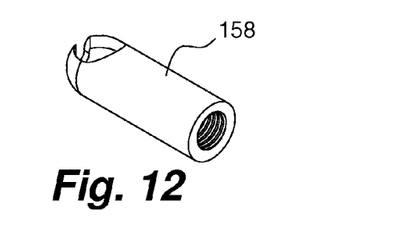
FIG. 12 is a diagrammatic perspective view of an embodiment of a hitch element of a syringe plunger rod.
Figure 13:
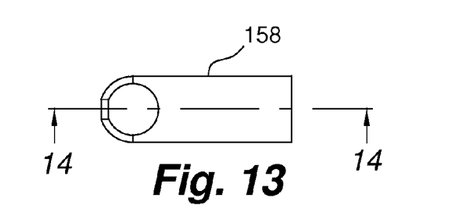
FIG. 13 is a diagrammatic top view of the hitch element shown in FIG. 12.
Figure 14:
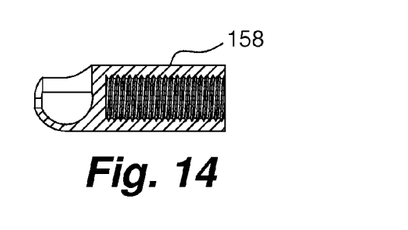
FIG. 14 is a diagrammatic cross-sectional view taken along line 14-14 of FIG. 13.
Figure 15:
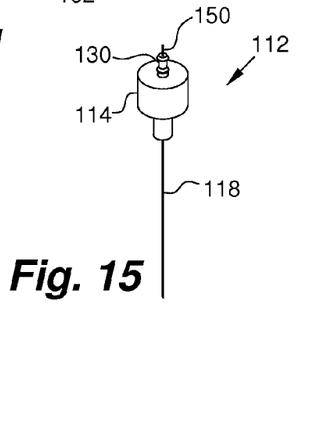
FIG. 15 is a diagrammatic perspective view of an embodiment of a needle hub assembly.
Figure 28:
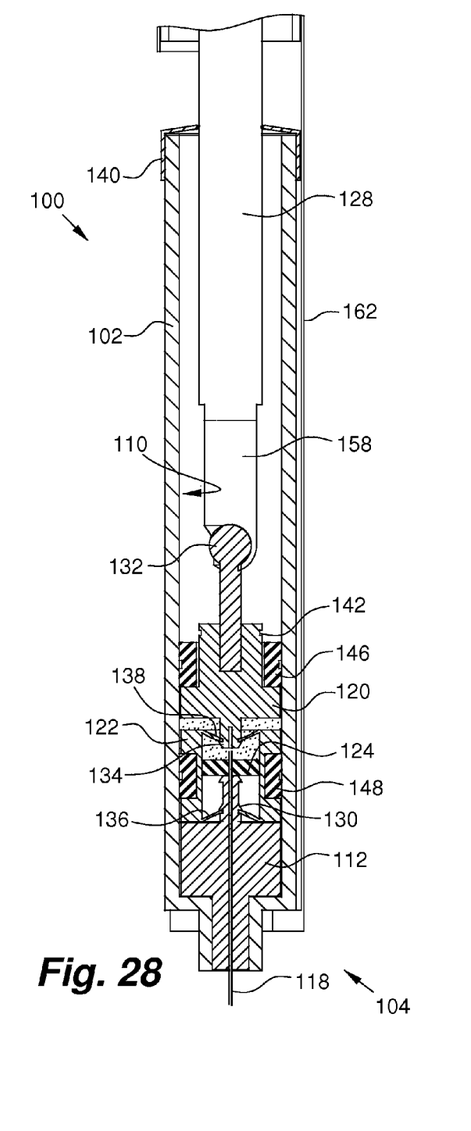
FIG. 28 is a diagrammatic partial cross-sectional view similar to that of FIG. 27, but wherein the plunger element has been fully actuated to the capture position.
Figure 29:
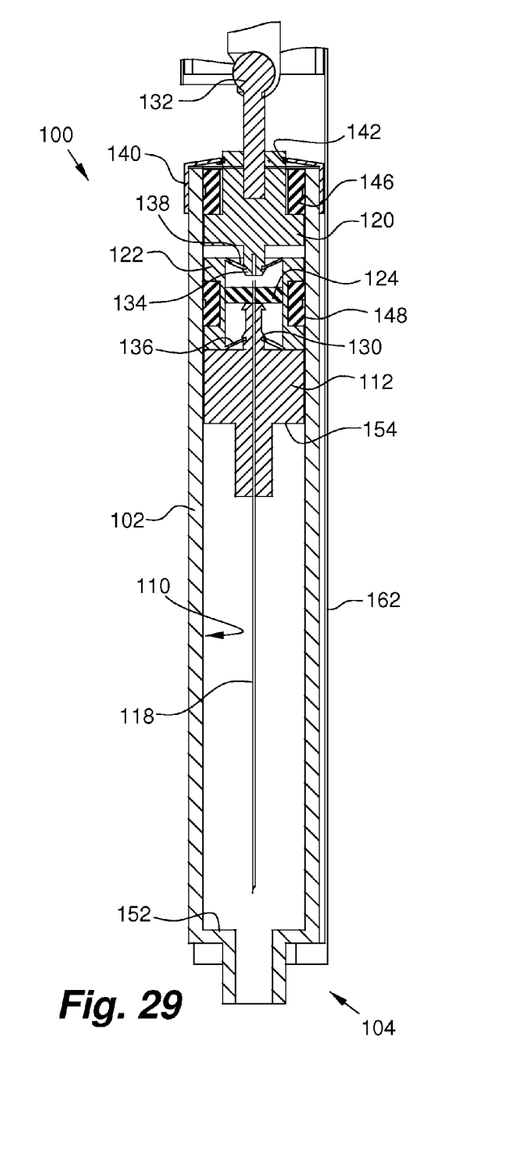
FIG. 29 is a diagrammatic partial cross-sectional view similar to that of FIG. 28, but wherein the plunger element has been fully actuated from the capture position to the safety position, thereby resulting in the needle hub assembly being transported from the injection position and secured in the retracted position.

A plunger element 120 is adapted to be in sealing engagement with the main bore 108 and axially actuatable therewithin between a ready position (as shown, for example, in FIG. 26), a capture position (as shown, for example, in FIG. 28) and a safety position (as shown, for example, in FIG. 29). In particular embodiments of a safety carpule system 100, the ready position and the safety position may be substantially the same. As illustrated, for example, in FIGS. 2, 3 and 7, certain preferred embodiments of a safety carpule system 100 are adapted to be laterally loaded into and laterally unloaded from a breech-loadable syringe assembly 156 having a syringe plunger rod 128 which is adapted to releasably engage the plunger element 120 such that the axial actuation of the plunger element 120 can be performed, typically exclusively, by way of the syringe plunger rod 128. As illustrated, for example, in FIGS. 2 and 11, this releasable engagement may be by way of, for example, relative lateral movement between an embodiment of a safety carpule system 100 and the syringe assembly 156. Put another way, the releasable engagement may be achievable by way of relative lateral movement between the syringe plunger rod 128 and the plunger element 120. Further, particular embodiments of a syringe assembly 156 adapted for use with particular embodiments of a safety carpule system 100 may comprise a hitch element 158. The hitch element 158 may be, for example, threadably connectable to the end of the syringe plunger rod 128. This hitch element 158, or similar structure, may be adapted to facilitate the releasable engagement between the syringe plunger rod 128 and the syringe rod engagement portion 132 of the plunger element 120. This engagement may have, for example, a releasable snap-fit.

A piston element 122 may include a diaphragm member 124, which may be formed (for example, molded) integrally or non-integrally with the piston element 122. The diaphragm member 124 is not limited to being a thin membrane, but can generally be, for example, any wall structure which is susceptible to being pierced or breached. The piston element 122 is typically adapted to be disposed within the main bore 108 and located generally between the needle hub assembly 112 and the plunger element 120. A fluid chamber 126 is generally defined by the volume within the main bore 108 between the plunger element 120 and the diaphragm member 124. The fluid chamber 126 is designed to be substantially filled with a liquid medication, such as an anesthetic. The piston element 122 is adapted to be in sealing engagement with the radial wall 110 and axially movable from a fluid retaining position (as shown, for example, in FIG. 26) to a fluid release position (as shown, for example, in FIG. 27) by way of an increase in a fluid pressure within the fluid chamber 126 resulting from the actuation of the plunger element 120 from the ready position toward the capture position.

Embodiments of a safety carpule system 100 are also envisioned in which the hub element 114 is in sealing engagement with the radial wall 110. In such embodiments, the piston element 122 may be in sealing engagement with the radial wall 110 by way of, for example, sealing engagement with an annular wall (not shown) of the hub element 114. Additionally, in further such embodiments, the piston element 122 may be substantially defined by the diaphragm member 124.

Figure 26:
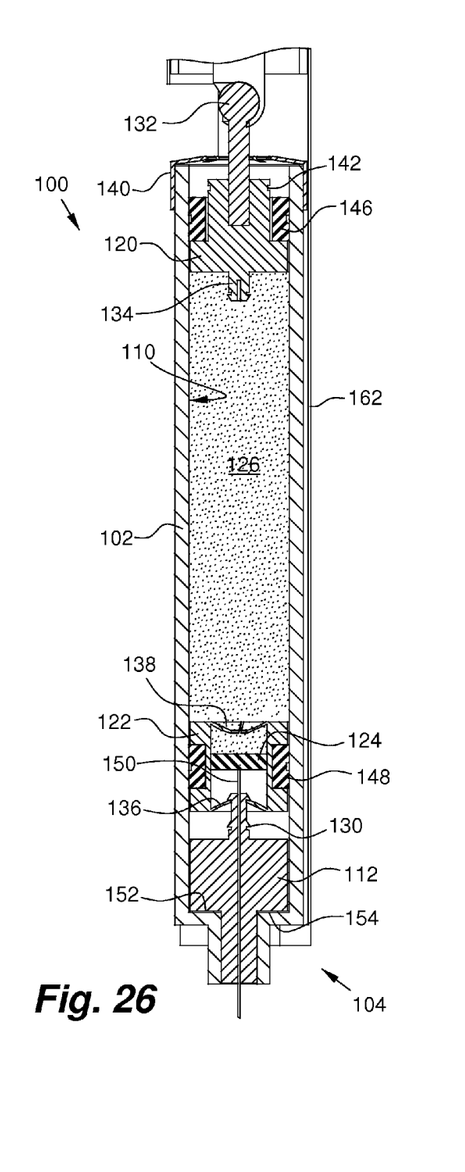
FIG. 26 is a diagrammatic partial cross-sectional view of the embodiment shown in FIG. 3, wherein the plunger element is in the ready position, the piston element is in the fluid retaining position, and the needle hub element is in the injection position.
Figure 27:
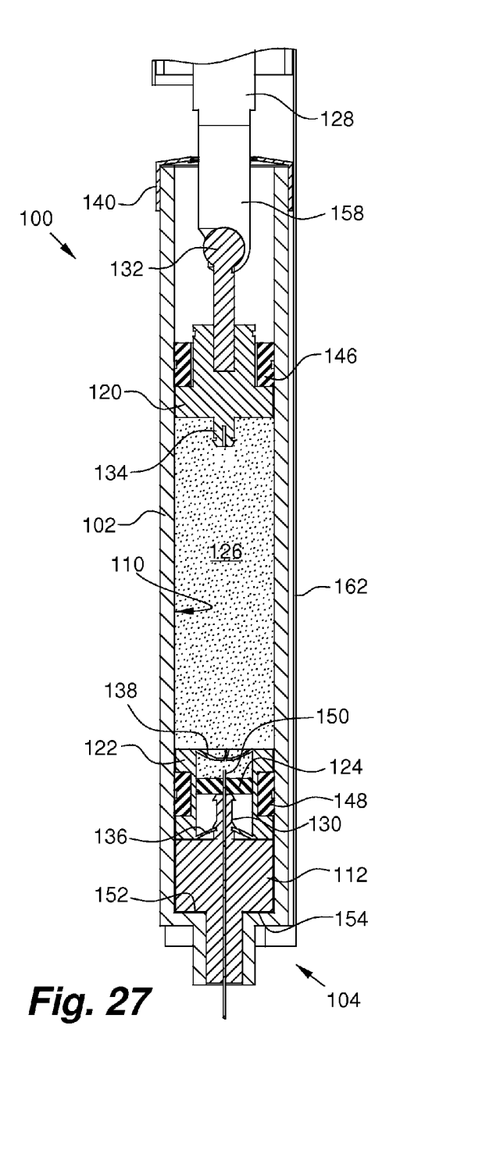
FIG. 27 is a diagrammatic partial cross-sectional view similar to that of FIG. 26, but wherein the plunger element has been partially actuated from the ready position toward the capture position, thereby increasing the fluid pressure within the fluid chamber and forcing the piston element into fluid release position.

As illustrated, for example, in FIG. 26, the piston element 122 prevents fluid communication between the fluid chamber 126 and the needle element 116 when the piston element 122 in the fluid retaining position. Conversely, as illustrated, for example, in FIG. 27, the diaphragm member 124 is punctured and allows fluid communication between the fluid chamber 126 and the needle element 116 when the piston element 122 is in the fluid release position. As illustrated, for example, in FIG. 27, in certain preferred embodiments of a safety carpule system 100, the diaphragm member is punctured by a rearward portion 150 of the needle element when the piston element 122 is in the fluid release position. In typical preferred embodiments of a safety carpule system 100, the hub element 114 does not have to be in sealing engagement with the radial wall 110, because the hub element 114 is typically not subject to direct exposure to liquid medication from the fluid chamber 126.

In certain embodiments of a safety carpule system 100, the respective sealing engagements may be by way of a plunger o-ring 146 radially disposed about the plunger element 120 and a piston o-ring 148 radially disposed about the piston element 122. Depending on the particular embodiment, the o-rings may or may not be formed (for example, molded) integrally with the plunger element 120 or the piston element 122, respectively. It is envisioned, for example, that in particular embodiments of a safety carpule system 100, one or both of the plunger element 120 and the piston element 122 may be made of a material which has sufficient sealing characteristics to sealingly engage the radial wall 110 of the main bore 108 without the need to incorporate o-rings manufactured as separate components.

Turning now to FIGS. 28 and 29 for illustration, the piston element 122 is simultaneously latchingly engageable by the needle hub assembly 112 and the plunger element 120 when the plunger element 120 is in the capture position such that actuation of the plunger element 120 from the capture position to the safety position results in the needle hub assembly 112 being transported from the injection position to the retracted position. FIG. 29 illustrates the needle hub assembly in a retracted position. The term "simultaneous latchingly engageable" does not mean that the respective latching engagements necessarily occur at the same time. In fact, in many preferred embodiments (such as, for example, the embodiment illustrated in operation between FIGS. 26 through 29), these latching engagements are neither initiated or completed simultaneously. Rather, the latching engagements of the piston element 122, once completed, may be maintained simultaneously.

In particular embodiments of a safety carpule system 100, the needle hub assembly 112 may include a first piston engagement portion 130. Similarly, the plunger element 120 may include a syringe rod engagement portion 132 and a second piston engagement portion 134, and the piston element 122 may include a hub engagement portion 136 and a plunger engagement portion 138. The syringe rod engagement portion 132 is for releasable engagement by a syringe plunger rod 128. The first piston engagement portion 130 is for latchable engagement with the hub engagement portion 136. The second piston engagement portion 134 is for latchable engagement with the plunger engagement portion 138. The term "latchable engagement" is generally intended to mean that once respective components are engaged (i.e., connected to each other), they remain engaged even when one of the respective components is then pulled in an axial direction opposite of the co-engaged component, for example along the main bore 108. Such an engagement may be established, for example, by way of a male-female frictional interface, ball and socket, annular snap, cantilever snap, the like, or a variation or combination thereof.

Figure 17:
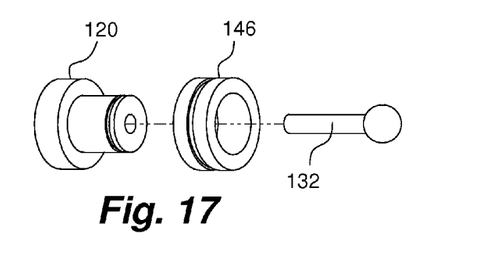
FIG. 17 is a diagrammatic exploded view of an embodiment of a plunger element with a plunger o-ring.
Figure 18:
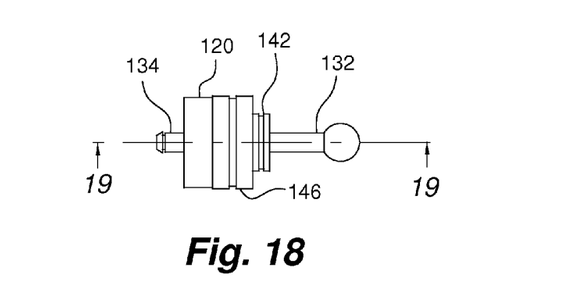
FIG. 18 is a diagrammatic side view of the plunger element shown in FIG. 17, but in assembled form.
Figure 19:
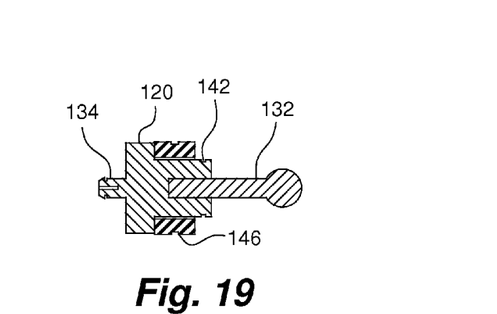
FIG. 19 is a diagrammatic cross-sectional view taken along line 19-19 of FIG. 18.
Figure 20:
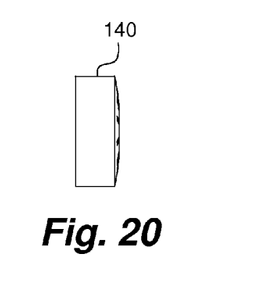
FIG. 20 is a diagrammatic side view of an embodiment of a safety catch element.
Figure 21:
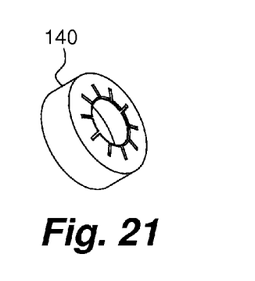
FIG. 21 is a diagrammatic perspective view of the safety catch element shown in FIG. 20.
Figure 22:
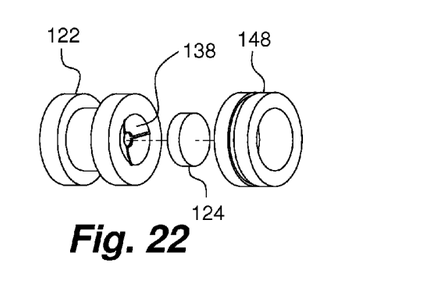
FIG. 22 is a diagrammatic exploded view of an embodiment of a piston element with a piston o-ring.
Figure 23:
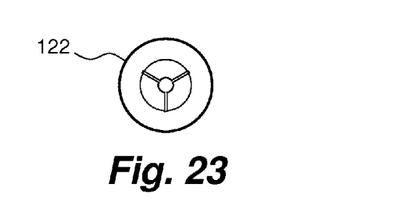
FIG. 23 is a diagrammatic end view of the piston element shown in FIG. 22, but in assembled form.
Figure 24:
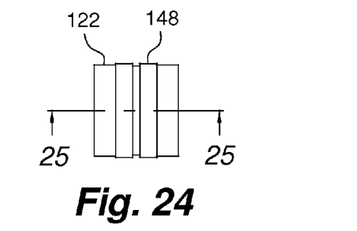
FIG. 24 is a diagrammatic side view of the piston element shown in FIG. 23.
Figure 25:
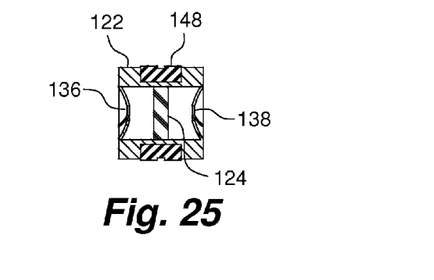
FIG. 25 is a diagrammatic cross-sectional view taken along line 25-25 of FIG. 24.

It is contemplated that the various engagement portions described herein may be initially formed integrally with or separately from the respective elements to which they are fixedly associated. For example, in FIGS. 9 and 17, the syringe rod engagement portion 132 is shown as separately-formed from the plunger element 120. However, in certain embodiments, the syringe rod engagement portion 132 may be formed integrally with the plunger element 120.

One example of an embodiment of a safety carpule system 100 with male-female type latching engagement is illustrated by the embodiments shown in the various figures. Turning to FIG. 28 for example, the first piston engagement portion 130 may be adapted for penetrating and thereby latchable engagement with the hub engagement portion 136. Similarly, the second piston engagement portion 134 may be adapted for penetrating and thereby latchable engagement with the plunger engagement portion 138.

Certain embodiments of a safety carpule system 100 may further comprise a safety catch element 140 adapted to be affixed to the housing element 102 at generally the second end 106 for latchingly engaging a catch detent 142 of the plunger element 120 upon the actuation of the plunger element 120 from the capture position (as shown, for example, in FIG. 28) into the safety position (as shown, for example, in FIG. 29) and thereby restricting the plunger element 120 from axial movement from the safety position toward the first end 104.

Figure 1:
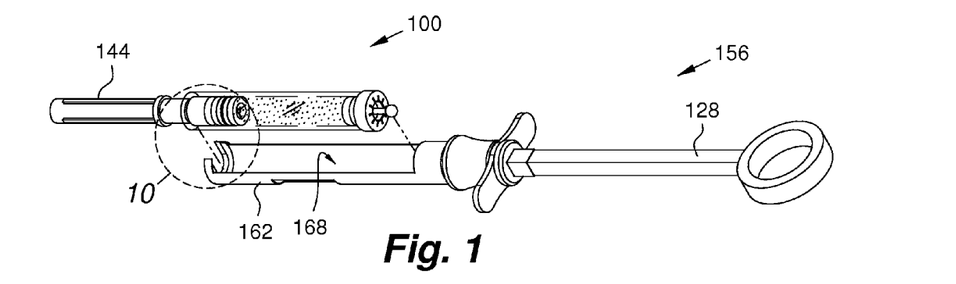
FIG. 1 is a diagrammatic perspective view of an embodiment of a safety carpule system and an associated syringe assembly prior to insertion of the safety carpule system into the breech of the syringe barrel.
Figure 2:
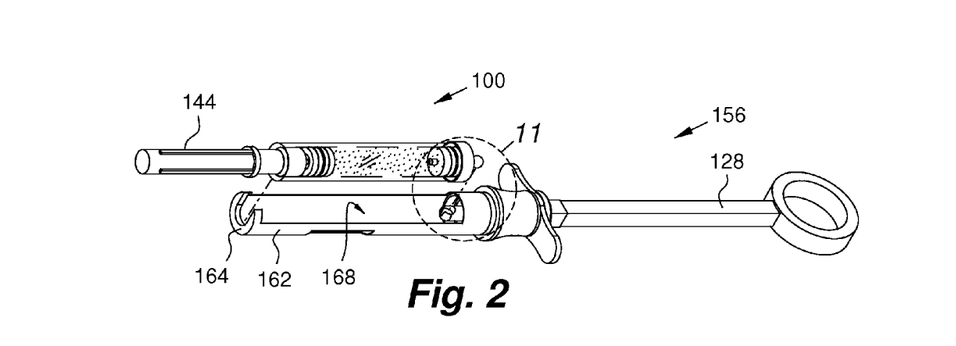
FIG. 2 is a further diagrammatic perspective view of the system and assembly shown in FIG. 1.
Figure 3:
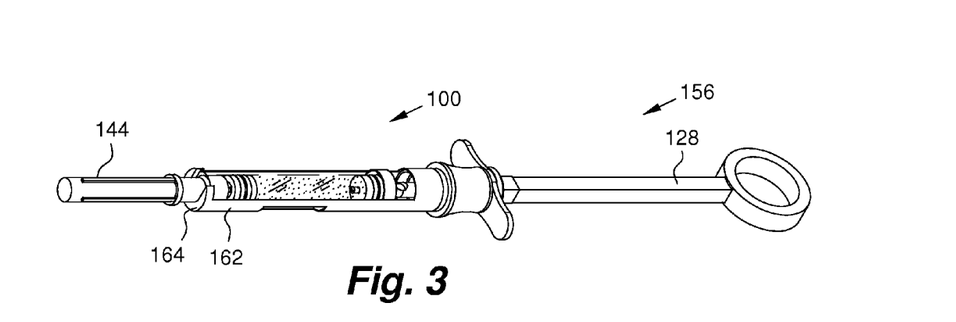
FIG. 3 is a diagrammatic perspective view of a safety carpule system and an associated syringe assembly after the insertion of the safety carpule system into the breech of the syringe barrel, the plunger element being in ready position.
Figures 4, 5, 6, 7:
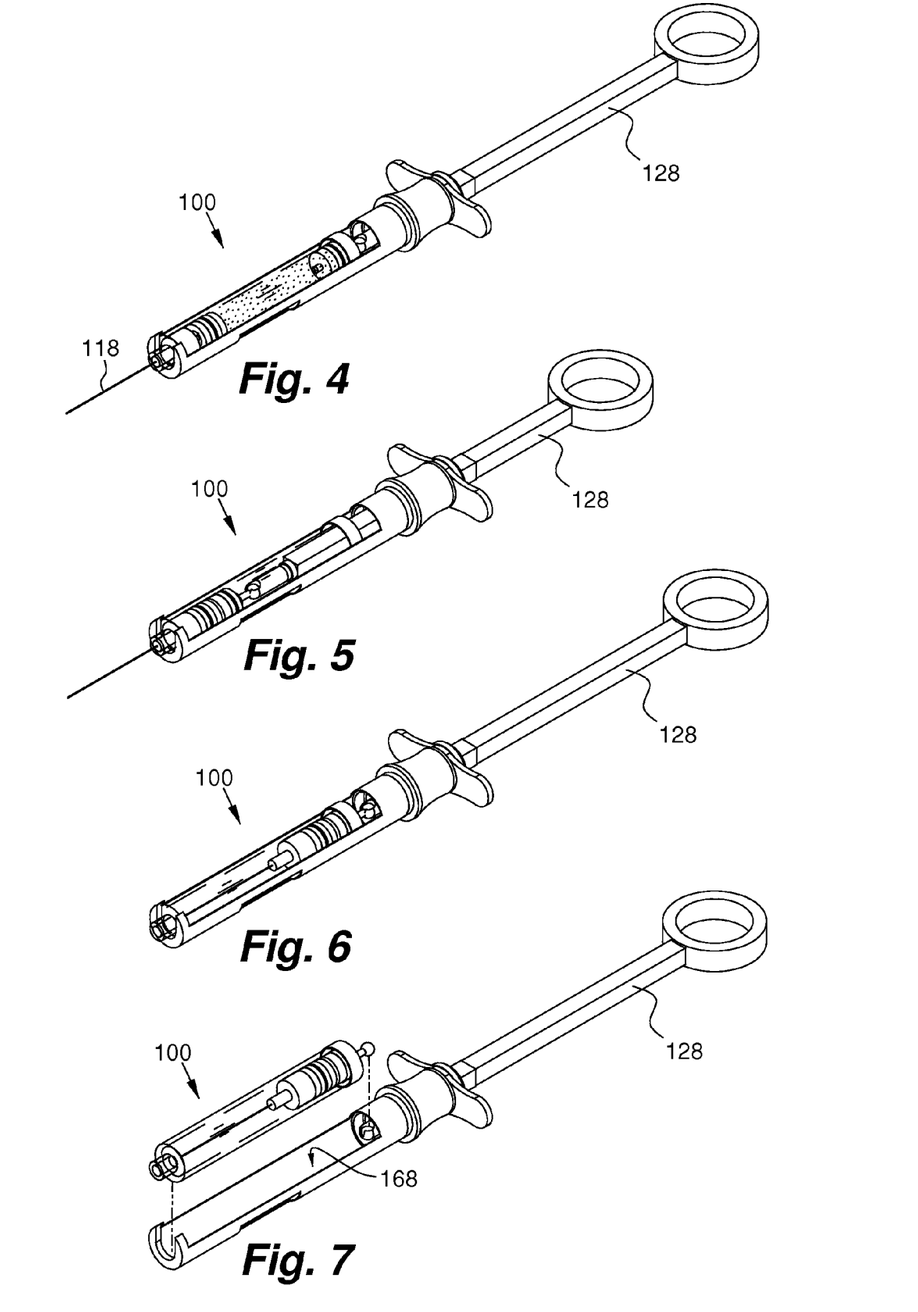
FIG. 4 is a diagrammatic perspective view of the system and assembly shown in FIG. 3, but in which the safety cap has been removed.
FIG. 5 is a diagrammatic perspective view of the system and assembly shown in FIG. 4, but in which the plunger element has been actuated from the ready position to the capture position and the medication has been dispensed.
FIG. 6 is a diagrammatic perspective view of the system and assembly shown in FIG. 5, but in which the plunger element has been actuated from the capture position to the safety position, thereby transporting the needle hub assembly to the retracted position.
FIG. 7 is a diagrammatic perspective view of the system and assembly shown in FIG. 6, but in which the safety carpule system has been removed from the breech of the syringe barrel and the needle hub assembly remains in the retracted position by way of the safety catch element.
Figures 8, 9:
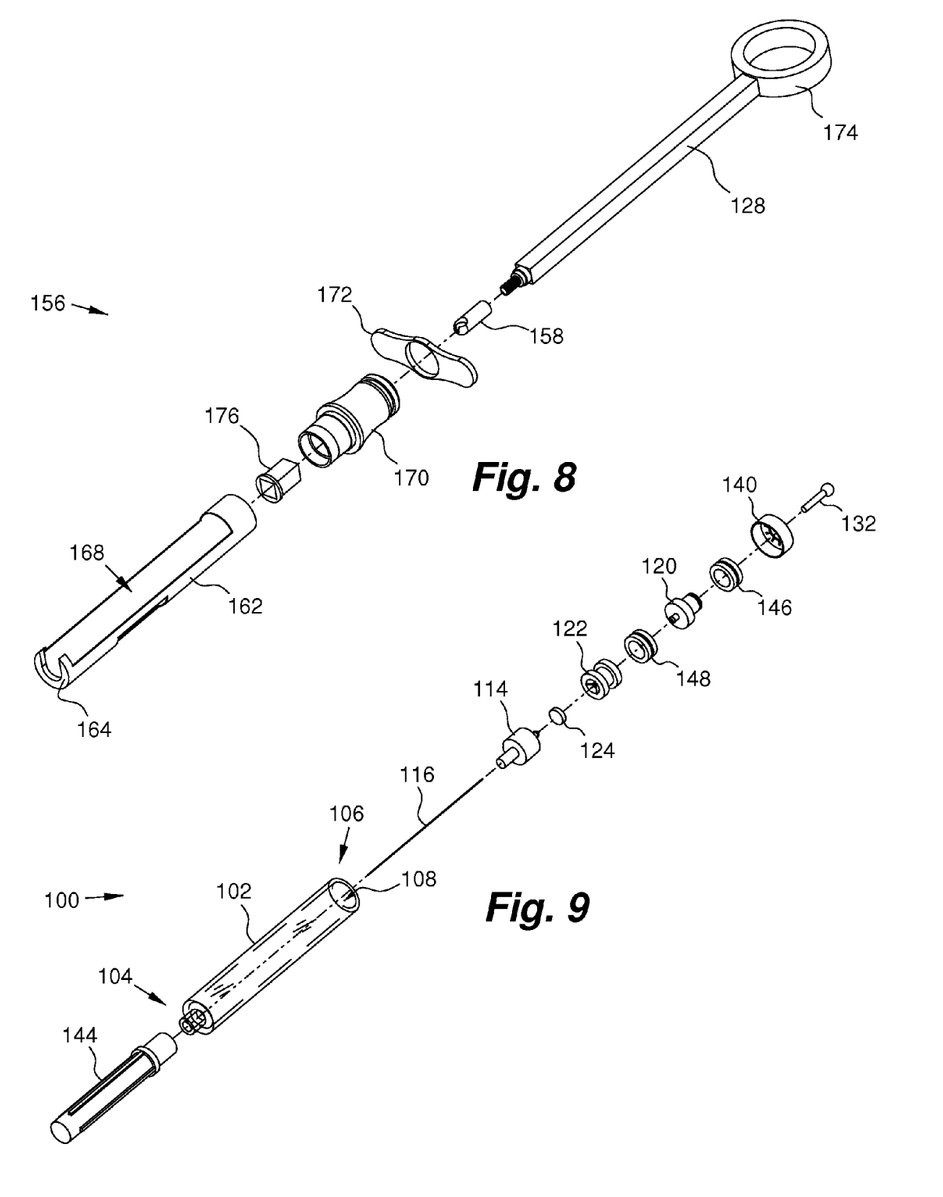
FIG. 8 is a diagrammatic exploded view of an embodiment of a syringe assembly adapted to receive and operate an embodiment of a safety carpule system.
FIG. 9 is a diagrammatic exploded view of an embodiment of a safety carpule system.

Embodiments of the safety carpule system 100 typically further comprise a safety cap 144 for removably engaging the housing element 102 at generally the first end 104 and substantially encapsulating the forward portion 118 of the needle element 116 when the needle hub assembly 112 is in the injection position (as shown, for example, in FIGS. 1, 2 and 26). Referring to FIGS. 3 and 9 for illustration, the safety cap 144 may be adapted to removably engage a neck portion 160 of the housing element at generally the first end and substantially encapsulating the forward portion when the needle hub assembly is in the injection position.

Figure 10:
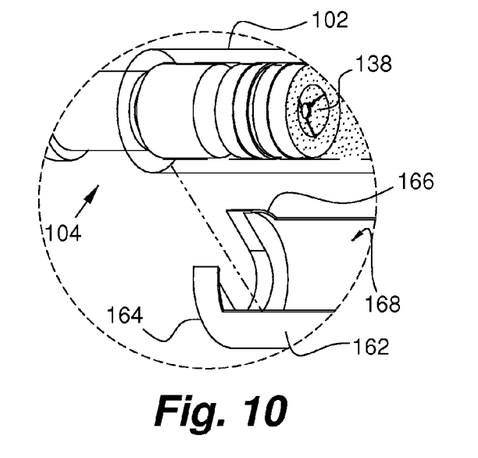
FIG. 10 is a diagrammatic enlarged view of detail 10 in FIG. 1.

Referring now to FIG. 10 for illustration, the syringe barrel 162 may have a lateral detent member 166 at generally the proximal end 164 for releasably engaging the first end 104 of the housing element 102 to secure the first end 104 from lateral movement outward of the breech opening 168 when the first end 104 is in releasable engagement with the lateral detent member 166. In typical operation with a breech-loadable syringe assembly 156 having a lateral detent member 166 similar to that which is illustrated in FIG. 10, an embodiment of a safety carpule system 100 may be placed into the breech opening 168 beginning with the first end 104 of the housing element 102. Once the first end 104 has entered the breech opening 168, it is moved axially along the syringe barrel 162 toward the proximal end 164 and into engagement with the lateral detent member 166. The safety carpule system 100 is then slightly rotated to place the plunger element 120 into releasable engagement with the syringe plunger rod 128, thereby bringing the housing element 102 into substantial axial alignment with the syringe barrel 162. The safety carpule system 100 is now loaded into the syringe for use in a dental or medical procedure.

Once the safety carpule system 100 is loaded into a syringe, the safety cap 144 may be removed, and the liquid medication within the safety carpule system 100 may be injected into a patient by way of the forward portion 118 of the needle element 116. Once the syringe plunger rod 128 has been axially compressed and the medication has been expended, the syringe plunger rod 128 can be returned to its uncompressed position, resulting in the needle hub assembly 112 being retracted completely into the housing element 102. The plunger element 120 can then be disengaged from the syringe plunger rod 128, and the safety carpule system 100 removed from the breech opening 168 for safe handling and disposal with or without replacement of the safety cap 144.

The foregoing detailed description of the invention is intended to be illustrative and is not intended to limit the scope of the invention. Changes and modifications are possible with respect to the embodiments detailed in the foregoing descriptions, and it is understood that the invention may be practiced otherwise than that specifically described herein and still be within the scope of the appended claims.

What is claimed is:

1. A safety carpule system with integral retractable needle, the safety carpule system comprising:
    a housing element being substantially cylindrical and including a first end, a second end and a main bore extending axially therebetween, the main bore having a radial wall;
    a needle hub assembly including a hub element and a needle element extending generally therethrough, the needle hub assembly being axially transportable within the main bore between an injection position and a retracted position, a forward portion of the needle element extending outward of the first end when the needle hub assembly is in the injection position, the forward portion being disposed entirely within the housing element when the needle hub assembly is in the retracted position;
    a plunger element in sealing engagement with the main bore and axially actuatable therewithin between a ready position, a capture position and a safety position; and
    a piston element including a diaphragm member and being disposed within the main bore generally between the needle hub assembly and the plunger element, a fluid chamber being generally defined by the volume within the main bore between the plunger element and the diaphragm member, the piston element being in sealing engagement with the radial wall and being axially movable from a fluid retaining position to a fluid release position by way of an increase in a fluid pressure within the fluid chamber resulting from the actuation of the plunger element from the ready position toward the capture position, the piston element preventing fluid communication between the fluid chamber and the needle element when in the fluid retaining position, the diaphragm member being punctured and allowing fluid communication between the fluid chamber and the needle element when the piston element is in the fluid release position, the piston element being simultaneously latchingly snap engageable by the needle hub assembly and the plunger element when the plunger element is in the capture position such that actuation of the plunger element from the capture position to the safety position results in the needle hub assembly being transported from the injection position to the retracted position.

2. The safety carpule system as defined in claim 1 in which the plunger element is releasably engageable by a syringe plunger rod such that the axial actuation can be performed by way of the syringe plunger rod, the releasable engagement being achievable by way of relative lateral movement between the syringe plunger rod and the plunger element.

3. The safety carpule system as defined in claim 1 in which the needle hub assembly includes a first piston engagement portion, the plunger element includes a syringe rod engagement portion and a second piston engagement portion, and the piston element includes a hub engagement portion and a plunger engagement portion, the syringe rod engagement portion being for releasable engagement by a syringe plunger rod, the first piston engagement portion being for latchable snap engagement with the hub engagement portion, and the second piston engagement portion being for latchable engagement with the plunger engagement portion.

4. The safety carpule system as defined in claim 1 further comprising a safety catch element affixed to the housing element at generally the second end for latchingly engaging a catch detent of the plunger element upon the actuation of the plunger element from the capture position into the safety position and thereby restricting the plunger element from axial movement from the safety position toward the first end.

5. The safety carpule system as defined in claim 1 further comprising a safety cap for removably engaging the housing element at generally the first end and substantially encapsulating the forward portion when the needle hub assembly is in the injection position.

6. The safety carpule system as defined in claim 1 in which the respective sealing engagements are by way of a plunger o-ring radially disposed about the plunger element and a piston o-ring radially disposed about the piston element.

7. The safety carpule system as defined in claim 1 in which the diaphragm member is punctured by a rearward portion of the needle element when the piston element is in the fluid release position.

8. The safety carpule system as defined in claim 1 in which the fluid chamber is substantially filled with a liquid medication.

9. The safety carpule system as defined in claim 8 in which the liquid medication is an anesthetic.

10. The safety carpule system as defined in claim 1 in which the housing element includes a hub seat for engaging a shoulder portion of the hub element to restrict axial movement of the hub element outward of the first end when the needle hub assembly is in the injection position.

11. The safety carpule system as defined in claim 1 adapted to be loaded into a breech-loadable syringe assembly having a syringe plunger rod in which the syringe plunger rod is adapted to releasably engage the plunger element such that the axial actuation can be performed by way of the syringe plunger rod.

12. The safety carpule system as defined in claim 1 in which the ready position and the safety position are substantially the same.

13. A safety carpule system with integral retractable needle, the safety carpule system comprising:
    a housing element being substantially cylindrical and including a first end, a second end and a main bore extending axially therebetween, the main bore having a radial wall;
    a needle hub assembly including a hub element and a needle element extending generally therethrough, the needle hub assembly being axially transportable within the main bore between an injection position and a retracted position, a forward portion of the needle element extending outward of the first end when the needle hub assembly is in the injection position, the forward portion being disposed entirely within the housing element when the needle hub assembly is in the retracted position;

a plunger element in sealing engagement with the main bore and axially actuatable therewithin between a ready position, a capture position and a safety position; and a piston element including a diaphragm member and being disposed within the main bore generally between the needle hub assembly and the plunger element, a fluid chamber being generally defined by the volume within the main bore between the plunger element and the diaphragm member, the fluid chamber being substantially filled with a liquid medication, the piston element being in sealing engagement with the radial wall and being axially movable from a fluid retaining position to a fluid release position by way of an increase in a fluid pressure within the fluid chamber resulting from the actuation of the plunger element from the ready position toward the capture position, the piston element preventing fluid communication between the fluid chamber and the needle element when in the fluid retaining position, the diaphragm member being punctured by a rearward portion of the needle element and thereby allowing fluid communication between the fluid chamber and the needle element when the piston element is in the fluid release position, the piston element being simultaneously latchingly snap engageable by the needle hub assembly and the plunger element when the plunger element is in the capture position such that actuation of the plunger element from the capture position to the safety position results in the needle hub assembly being transported from the injection position to the retracted position.

14. The safety carpule system as defined in claim 13 in which the liquid medication is an anesthetic.

15. The safety carpule system as defined in claim 14 in which the needle hub assembly includes a first piston engagement portion, the plunger element includes a syringe rod engagement portion and a second piston engagement portion, and the piston element includes a hub engagement portion and a plunger engagement portion, the syringe rod engagement portion being for releasable engagement by a syringe plunger rod, the first piston engagement portion being for latchable engagement with the hub engagement portion, the second piston engagement portion being for latchable engagement with the plunger engagement portion.

16. The safety carpule system as defined in claim 14 further comprising a safety catch element affixed to the housing element at generally the second end for latchingly engaging a catch detent of the plunger element upon the actuation of the plunger element from the capture position into the safety position and thereby restricting the plunger element from axial movement from the safety position toward the first end.

17. The safety carpule system as defined in claim 14 further comprising a safety cap for removably engaging the housing element at generally the first end and substantially encapsulating the forward portion when the needle hub assembly is in the injection position.

18. A safety carpule system with integral retractable needle, the safety carpule system comprising:

a housing element being substantially cylindrical and light permeable and including a first end, a second end and a main bore extending axially therebetween, the main bore having a radial wall;

a needle hub assembly including a hub element and a needle element extending generally therethrough, the needle hub assembly being axially transportable within the main bore between an injection position and a retracted position, a forward portion of the needle element extending outward of the first end when the needle hub assembly is in the injection position, the forward portion being disposed entirely within the housing element when the needle hub assembly is in the retracted position;

a plunger element in sealing engagement with the main bore and axially actuatable therewithin between a ready position, a capture position and a safety position, the plunger element being releasably engageable by a syringe plunger rod such that the axial actuation can be performed by way of the syringe plunger rod, the releasable engagement being achievable by way of relative lateral movement between the syringe plunger rod and the plunger element;

a piston element including a diaphragm member and being disposed within the main bore generally between the needle hub assembly and the plunger element, a fluid chamber being generally defined by the volume within the main bore between the plunger element and the diaphragm member, the fluid chamber being substantially filled with a liquid medication, the piston element being in sealing engagement with the radial wall and being axially movable from a fluid retaining position to a fluid release position by way of an increase in a fluid pressure within the fluid chamber resulting from the actuation of the plunger element from the ready position toward the capture position, the piston element preventing fluid communication between the fluid chamber and the needle element when in the fluid retaining position, the diaphragm member being punctured by a rearward portion of the needle element and thereby allowing fluid communication between the fluid chamber and the needle element when the piston element is in the fluid release position, the piston element being simultaneously latchingly engageable by the needle hub assembly and the plunger element when the plunger element is in the capture position such that actuation of the plunger element from the capture position to the safety position results in the needle hub assembly being transported from the injection position to the retracted position;

a safety catch element affixed to the housing element at generally the second end for latchingly engaging a catch detent of the plunger element upon the actuation of the plunger element from the capture position into the safety position and thereby restricting the plunger element from axial movement from the safety position toward the first end; and a safety cap for removably engaging a neck portion of the housing element at generally the first end and substantially encapsulating the forward portion when the needle hub assembly is in the injection position.

19. The safety carpule system as defined in claim 18 in which the needle hub assembly includes a first piston engagement portion, the plunger element includes a syringe rod engagement portion and a second piston engagement portion, and the piston element includes a hub engagement portion and a plunger engagement portion, the syringe rod engagement portion being for releasable engagement by a syringe plunger rod, the first piston engagement portion being for penetrating and thereby latchable engagement with the hub engagement portion, the second piston engagement portion being for penetrating and thereby latchable engagement with the plunger engagement portion.

20. The safety carpule system as defined in claim 18 further comprising a breech-loadable syringe assembly, the breech loadable syringe assembly including the syringe plunger rod, a syringe barrel with a breech opening and a proximal end, the breech opening being adapted to substantially laterally receivingly engage the housing element, the syringe barrel having a lateral detent member at generally the proximal end for releasably engaging the first end to secure the first end from lateral movement outward of the breech opening when the first end is in the releasable engagement with the lateral detent member.

* * * * *